United States Patent [19]

Malmin

[11] Patent Number: 4,491,134
[45] Date of Patent: Jan. 1, 1985

[54] HAIR REPLACEMENT APPARATUS

[76] Inventor: Oscar Malmin, 127 E. Wayne Ave., Akron, Ohio 44301

[21] Appl. No.: 249,199

[22] Filed: Mar. 30, 1981

Related U.S. Application Data

[60] Continuation-in-part of Ser. No. 190,664, Sep. 25, 1980, abandoned, which is a division of Ser. No. 932,513, Aug. 10, 1978, Pat. No. 4,263,913.

[51] Int. Cl.³ .............................................. A61F 1/00
[52] U.S. Cl. .................................................... 128/330
[58] Field of Search ................. 128/330, 340, 339; 3/1; 46/172; 132/53, 5; 223/104; 112/169

[56] References Cited

U.S. PATENT DOCUMENTS

| | | | |
|---|---|---|---|
| 527,263 | 10/1894 | Blanchard | 128/339 |
| 1,059,631 | 4/1913 | Popovics | |
| 2,253,535 | 1/1940 | Mann | 46/172 |
| 2,636,460 | 4/1953 | Seiderman | 112/1 |
| 3,062,214 | 11/1962 | Maxwell | 128/330 |
| 3,119,398 | 1/1964 | Bennett | 132/5 |
| 3,421,521 | 1/1969 | Rich | 132/5 |
| 3,513,860 | 5/1970 | Kost | 132/5 |
| 3,553,737 | 1/1971 | Bauman | 3/1 |
| 3,589,376 | 6/1971 | Kohler | 132/5.53 |
| 3,596,292 | 7/1971 | Erb | 3/1 |
| 3,608,095 | 9/1971 | Barry | 3/1 |
| 3,699,969 | 10/1972 | Allen | 128/330 |
| 3,755,824 | 9/1973 | Sperling | 3/1 |
| 3,845,772 | 11/1974 | Smith | 128/335 |
| 3,858,245 | 1/1975 | Nate | 128/329 |
| 3,877,570 | 4/1975 | Barry | 206/63.3 |
| 3,908,674 | 9/1975 | Kessler | 132/53 |
| 3,914,801 | 10/1975 | Dick | 128/335.5 |
| 4,027,675 | 6/1977 | Colone | 3/1 |
| 4,054,954 | 10/1977 | Nakayama | 3/1 |
| 4,126,124 | 11/1978 | Miller | 128/330 X |
| 4,221,212 | 9/1980 | Miller | 128/330 X |
| 4,314,565 | 2/1982 | Lee | 128/754 X |

FOREIGN PATENT DOCUMENTS 30751 3/1920 Norway .

Primary Examiner—Michael H. Thaler
Attorney, Agent, or Firm—Reese Taylor

[57] ABSTRACT

A method of treating baldness is disclosed which includes the implantation of strands of natural or artificial hair beneath the scalp and into the subcutaneous tissue. The method contemplates pre-forming the strands of hair into a U-shaped loop which can be implaced beneath the scalp by means of a penetration instrument in an arcuate or concave configuration with respect to the scalp for improved retention properties. Apparatus is also disclosed for carrying out the method which will facilitate engaging and implanting the hair in the manner just described and which is also capable of readily disengaging the hair from the penetration instrument for removal of the instrument and which is further capable of injecting tissue adhesives and hemostatic agents into the tissue surrounding the hair to stabilize it and assist the healing and anchoring process. It is also possible to perform the method of this invention without pre-forming the strand except to the extent that it is formed when placed on the penetration instrument.

1 Claim, 19 Drawing Figures ated application Ser. No. 190,664, filed
HAIR REPLACEMENT APPARATUS

RELATED APPLICATIONS

This application is a continuation-in-part of Applicant's earlier filed application Ser. No. 190,664, filed Sept. 25, 1980, now abandoned, which is a division of Applicant's earlier filed application Ser. No. 932,513, filed Aug. 10, 1978, now U.S. Pat. No. 4,263,913.

FIELD OF THE INVENTION

This invention relates, in general, to a method and apparatus for treating baldness and in particular relates to a method and apparatus wherein the replacement hair can be firmly and securely implanted beneath the scalp to resist inadvertent dislodgement and can be implanted in a particular fashion so that the portions of the replacement hair projecting above the scalp assume natural positions.

PRIOR ART STATEMENT

In general, hairpieces have long been known as one method of solving the problem of baldness. There are also a number of other known treatments and methods of correcting baldness, but problems with poor appearance and defective anchoring have been encountered.

Such methods have involved implanting various retaining devices such as, for example, specially treated wires or sutures into the scalp with portions thereof being exposed and with the exposed portions forming a network to which strands of natural or synthetic hair can be tied or woven. Difficulties have developed with these methods, however, with regard to infection and also to the requirement for periodic tightening or reweaving.

Still further methods have involved cutting a circular plug containing hair follicles from a donor site and transplanting that plug into a prepared recipient site in the bald area. There is a high rate of rejection with this method however.

Additional methods have involved the general concept of embedding synthetic fibers or natural hair into the scalp but a severe problem with regard to anchoring the fibers has been encountered leading to a high failure rate which is believed to be caused by an inability to resist the healing forces for any reasonably long period or due to secondary infection, with a consequent expulsion or rejection of the embedded hair.

With regard to the patent prior art, there are a large number of patents in existence and known to Applicant relating to this general field many of which reflect various of the aforementioned methods.

Bauman U.S. Pat. No. 3,553,737 illustrates one of the "weaving" methods and discloses one of the methods above referred to wherein an anchor member, in the form of a continuous suture, is embedded into the scalp to which a web is attached following which the hair can be attached to the web.

Barry U.S. Pat. No. 3,608,095 is illustrative of the "hairpiece" methods and discloses the placing of loops in the scalp to which a hairpiece can be attached.

Allen U.S. Pat. No. 3,699,969 discloses a hair implant method of one of the types generally referred to above wherein a plug of natural or synthetic fibers is inserted directly into the scalp by means of a concentric dual needle arrangement relying, however, on acceptance of the implanted plug.

Nate U.S. Pat. No. 3,858,245 discloses the utilization of individual suture loops which are sewn into the scalp and serve as anchors for attaching wefts of hair similar to Bauman.

Dick U.S. Pat. No. 3,914,801 also discloses forming suture loops in concentric circles on the scalp following which wefts of hair may be attached thereto.

Colone, U.S. Pat. No. 4,027,675 discloses the implanting of loops of hair into the subcutaneous portion of the head with the ends of adjacent loops being tied together. However, these points of interconnection are external and would present obvious problems in grooming the hair.

Erb U.S. Pat. No. 3,596,292 discloses a hair implant method where the implanted hair has a percutaneous portion having elastic properties and a divergent cross-section for anchoring purposes.

Bennett U.S. Pat. No. 3,119,393 also discloses an implanting method wherein single strands of hair are processed so as to provide a nearly natural root structure to again assist in anchoring.

Popovics U.S. Pat. No. 1,059,631 primarily discloses an instrument for implanting hairs directly into the scalp in which small hooks are used to retain the hair.

Maxwell U.S. Pat. No. 3,062,214 also discloses apparatus for implanting the fibers, and particularly the ends thereof, directly into the scalp.

Barry U.S. Pat. No. 3,877,570 is another of the "hairpiece" approaches and discloses a sterile suture suitable for attaching hairpieces to the scalp.

Kost U.S. Pat. No. 3,513,860 discloses another method in which the hair is formed into U-shaped loops and the bases of the loops are pushed into the conventional base of a hairpiece in a straight line perpendicular to the base and applying adhesive or curing the base for permanent anchoring.

Smith U.S. Pat. No. 3,845,772 discloses a retention suture which possibly could be utilized in connection with treating baldness to prevent tearing of tissue when closing an incision, but is silent with regard to anchoring the actual strands beneath the scalp.

Kessler U.S. Pat. No. 3,908,674 discloses a method of securing hairpieces to cover a bald area of the scalp wherein sutures are permanently implanted within the scalp and held by washers and the hairpiece is secured thereto.

Sperling U.S. Pat. No. 3,755,824 discloses another method for avoiding the appearance of baldness wherein sutures are located permanently at strategic locations on the scalp and a scalp net is secured thereto.

Kohler U.S. Pat. No. 3,589,376 is essentially directed to a method of making wigs.

Rich U.S. Pat. No. 3,421,521 is also directed to a method of forming a hairpiece per se as in Mann U.S. Pat. No. 2,253,635.

Seiderman U.S. Pat. No. 2,636,460 discloses a process for manufacturing products simulating human or animal hair and its only pertinency is the fact that bunched loops are inserted into the base or scalp portion of the head using a trocar means.

Norweigan Pat. No. 30,751 is of some interest also in that two hairs are joined together at their root ends by a gold wire.

Nakayama U.S. Pat. No. 4,054,954 is also of interest in showing an endless suture which is embedded under the scalp and a plurality of rings threaded onto the suture which serve as anchoring means for a hairpiece.

While this prior art is illustrative of the several known methods of treating baldness, none of them however disclose the unique method disclosed herein by Applicant wherein the hair can be firmly and securely implanted in the subcutaneous tissue beneath the scalp with its projecting ends assuming a relatively normal disposition above the surface of the scalp.

SUMMARY OF THE INVENTION

It has been found that improved results can be obtained in connection with the implantation of natural or artificial replacement hair by preferably pre-forming the strands of the hair to a looped or U-shaped configuration; securing the loop just formed to a penetration instrument or needle; inserting that instrument beneath the scalp in a curved path; disposing the strand of hair in the tissue in a more or less concave configuration with regard to the surface of the scalp and withdrawing of the needle.

It has also been found that this method can further be facilitated by applying a tissue adhesive to the base of the loop so as to assist in anchoring the same in the tissue.

Furthermore, it has been found that carrying out a method of this nature can be facilitated by providing a needle having a handle and an arcuate projecting end terminating in a sharp point capable of penetrating the scalp. It has also been discovered that a pocket can be provided rearwardly from the pointed end to receive the strands of hair and carry it into the tissue.

Furthermore, it has been discovered that a gripping handle can be employed to increase the mechanical advantage and precison of the operation by engaging the handle end of the needle.

It has also been discovered that provision of a hollow needle and hollow gripping handle will facilitate attachment of the gripping handle to a source of tissue adhesive or hemostatic fluid so that such fluid can be injected through the handle and the needle into the tissue adjacent the location of the implanted hair.

Furthermore, it has also been discovered that further improved results can be obtained by providing means for removing the hair from the carrying notch on the needle so as to insure that it remains in place upon withdrawal of the needle.

Accordingly then, production of an improved method and apparatus for treating baldness becomes the principal object of this invention with other objects hereof becoming more apparent upon a reading of the following brief specification considered and interpreted in view of the accompanying drawings.

OF THE DRAWINGS

BRIEF DESCRIPTION OF THE PREFERRED EMBODIMENTS

THE APPARATUS

It will first be noted that in describing the various embodiments of the method and apparatus of this invention reference will commonly be made to "strands" and it should be understood that in all instances such reference is intended to refer to both natural hair and synthetic fibers and is employed for the sake of brevity in this description.

Figure 1:
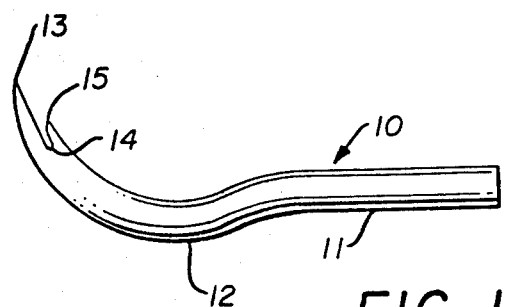
FIG. 1 is an elevational view of one form of needle employed in this invention.
Figure 4:
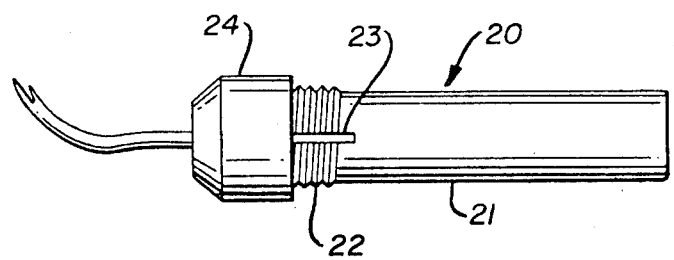
FIG. 4 is an elevational view showing the needle in place in the gripping handle.
Figure 11:
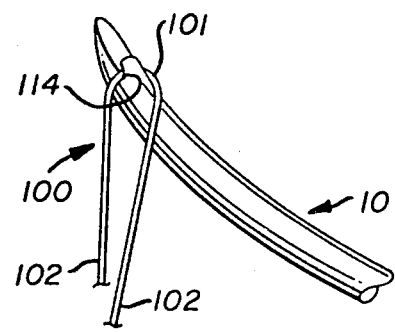
FIG. 11 is a perspective view showing the needle engaging a strand of hair.

Turning then to the drawings, it will be noted that the basic components of the apparatus necessary to carry out the method include a penetration instrument such as the needle 10 of FIG. 1, a gripping handle such as the handle 20 of FIG. 4 and the strand itself such as the strand 100 of FIG. 11.

Referring then to FIG. 1 for a description of the instrument or needle per se, it will be noted that the needle has an elongate shank portion 11 which terminates in an arcuate penetration portion 12 which in turn ultimately terminates in a pointed or beveled end 13. The needle is cut away rearwardly from the point 13 to form the pocket 14 with an overlying lip 15.

Figure 3:
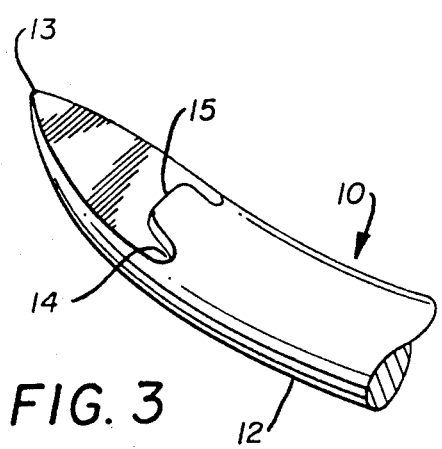
FIG. 3 is a partial perspective view of another form of the needle shown in FIG. 1.
Figure 2:
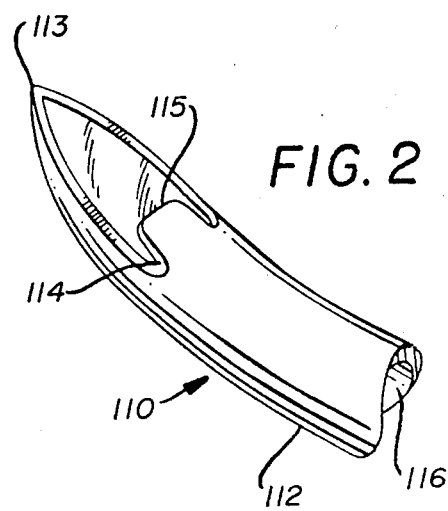
FIG. 2 is a partial perspective view of one form of the needle shown in FIG. 1.

The basic configuration of the needle is shown in FIG. 1 and reference will now be had to FIGS. 2 and 3 wherein partial perspective views are shown of the area adjacent the ultimate penetrating end 13 of two variations.

FIG. 3 shows a solid needle and the end 13 and penetration portion 12 are illustrated therein. FIG. 2 shows a hollow needle and in this instance the needle characteristics have been referred to by the numerals 110 through 116 with 116 indicating the hollow central bore or passageway. Similar characteristics are referred to by similar numbers in FIGS. 1 through 3 although numbers in the 100 series will be used throughout to refer to the hollow needle 110 while numerals in the 10 series will be used throughout to refer to the solid needle 10.

In any event, however, the basic components of the needle shown in FIGS. 2 and 3 are identical except for the fact that one is hollow and one is solid.

Figure 5:
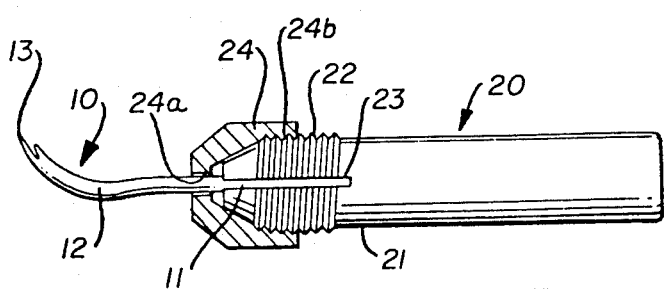
FIG. 5 is an elevational view similar to FIG. 4 partially in section.

Turning then to FIG. 4, it will be seen that a gripping handle 20 is provided with this handle having a body 21 terminating in a threaded end 22 and having opposed axially extending slots 23,23 therein. Only one of these slots is shown in the view of this handle in FIGS. 4 and 5, but essentially they are slots cut inwardly in an axial direction from the left hand end of the handle.

The handle also includes a cap 24 which has a through aperture 24a sized so as to fairly snugly receive the shank 11 of the needle 10. The cap 24 also is threaded internally as at 24b so that, with the shank 11 inserted into the front end of the handle 20 and through the opening 24a of cap 24, the cap can be screwed down so as to essentially collapse the end of the handle about the slots 23 and grip the shank in place. This provides a vise-like clamping arrangement so that the needle 10 is securely held in place.

Figure 6:
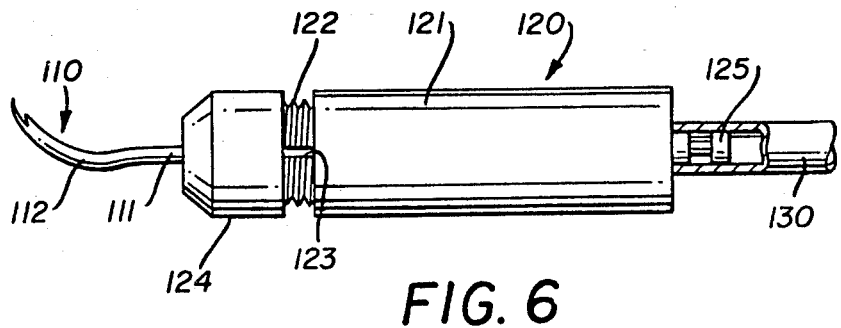
FIG. 6 is an elevational view of a modified form of gripping handle with the needle in place.
Figure 7:
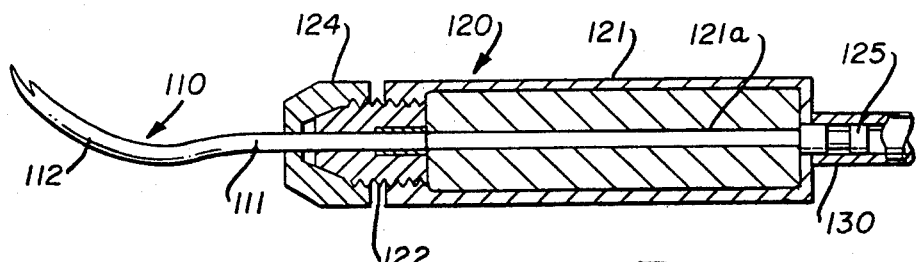
FIG. 7 is a view similar to FIG. 6 broken away in section.

FIGS. 6 and 7 show a modified form of the handle of the invention intended to be used with the hollow needle of FIG. 2. Thus the gripping handle 120 has a body 121, a threaded end 122 and the slots 123. The cap 124 of FIG. 6 is essentially identical to the cap 24 of FIG. 4 of the drawings and the shank 111 of needle 110 is intended to be inserted therein and clamped in place in the same manner described in connection with that drawing figure.

Reference to FIG. 7, however, will illustrate that the gripping handle 120 indeed does differ from the gripping handle of FIG. 4 in that it has a through interior passage 121a. Keeping in mind that the needle 110 is hollow it will be understood that when the needle is in place, the central bore 116 of the needle will be in fluid communication with the central bore 121a of the handle 120.

Furthermore, referring to FIGS. 6 and 7 it will be seen that a conventional snap type fitting 125 is received on the rear end of the handle 121. A hose or tube 130 can be snapped over this fitting 125 so that suitable fluid can be injected through the tubing 130, the passageway 121a and the needle 111 into the tissue as will be described subsequently. The source of the fluid is not illustrated herein.

Figure 8:
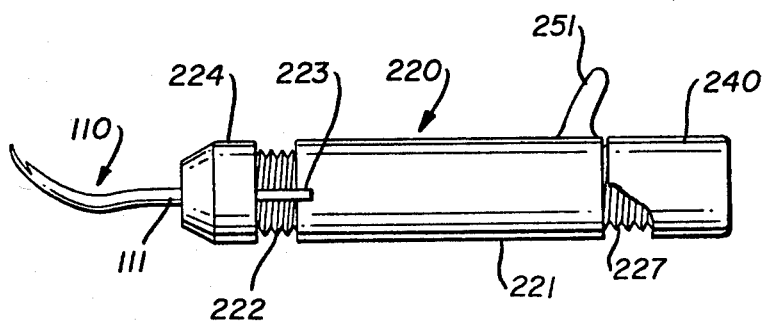
FIG. 8 is an elevational view of a further modified form of gripping handle with the needle in place.
Figure 9:
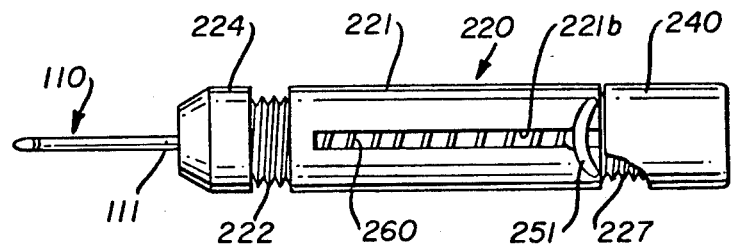
FIG. 9 is a top plan view of the gripping handle and needle assembly of FIG. 8.
Figure 10:
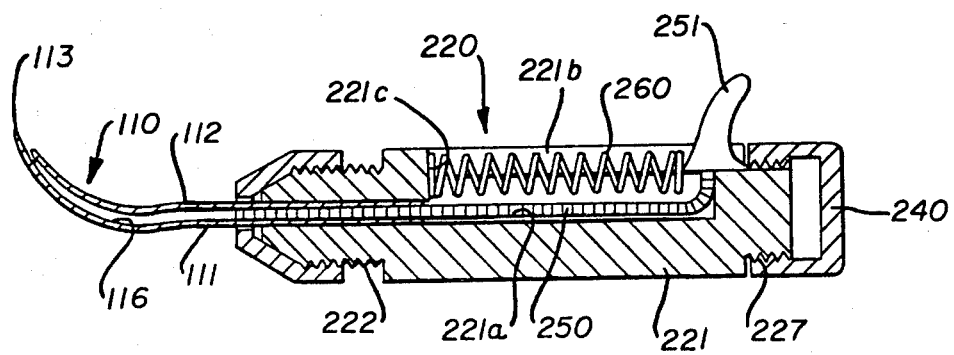
FIG. 10 is a view similar to FIG. 8 in section.

FIGS. 8, 9 and 10 illustrate yet another form of gripping handle 220 suitable for use in connection with the hollow needle 110.

The gripping handle 220 has a body 221, a threaded forward end 222 and the slots 223 which cooperate with the cap 224 to clamp the shank 111 of needle 110 in the handle as previously described.

This particular handle 220, however, has additional features not found in the handles of FIGS. 4 and 6.

For example, the rear end of the handle body 221 is threaded at 227 for receipt of a second cap 240. Referring to FIG. 9 it will be seen that an elongate slot 221b is also provided in the body 221 and that a movable handle 251 is slidably received in this slot. Referring to FIG. 10, it will be seen that a wire or stylet 250 is secured to the handle 251 passing through a central bore 221a and into the central bore of the hollow needle 110. This wire 250 is a flexible member such as chromel wire.

Also received within the interior of the body 221 is a spring 260 which butts against a shoulder 221c and against the movable handle 251. When the cap 240 is screwed on, all of this structure will be retained in place and in fact the components will be in the position illustrated in FIG. 10 of the drawings with the spring serving to retract handle 251 and wire 250 to the right of FIG. 10 of the drawings against the face of cap 240.

Obviously, thumb pressure or finger pressure on the handle 251 will compress the spring 260 and force the wire 250 to the left of FIG. 10 and through the hollow interior 116 of the needle 110 for purposes which will be described.

THE METHOD

Having described the apparatus necessary to carry out the method of the invention, the method itself will now be described.

Figure 16:
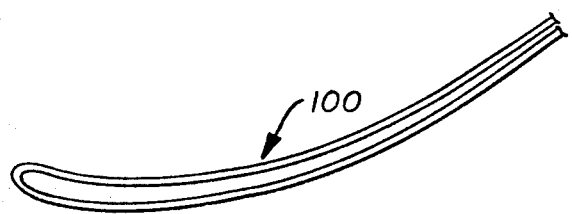
FIG. 16 is a view showing a pre-formed strand of hair according to this invention.

In the preferred method of this invention the strand 100 will be pre-formed to the configuration shown in FIG. 16. This step can be accomplished by a number of methods such as, for example, the application of heat. Regardless of whether natural or artificial hair is employed, it is believed that suitable methods are sufficiently known to enable this step to be performed.

This step also obtains several advantages. For one thing, using a pre-formed strand facilitates engagement with instrument 10 or 110. It also reduces the likelihood of crimping or deforming the strand during the insertion operation. Furthermore, this provides a relatively passive structure so that once it is in place in the tissue it will have a tendency to retain the desired configuration and avoid unnecessary irritation of the tissue.

Referring next then, for example, to FIG. 11 it will be seen how the needle 10 is capable of receiving the strand of hair 100, which is formed in the U-shaped loop configuration having a base 101 and free ends 102,102 in the notch 14.

Figure 12:
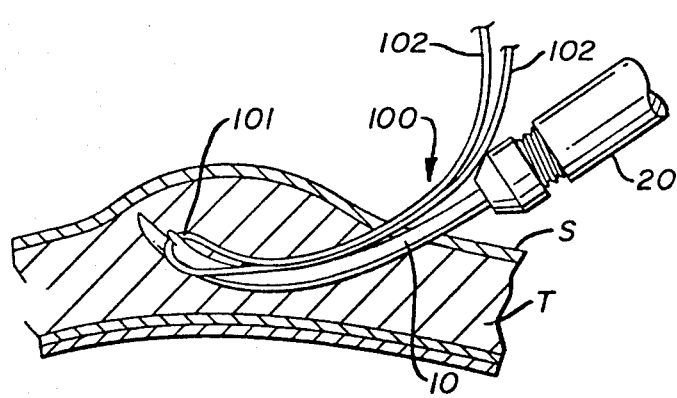
FIG. 12 is a sectional view showing the implantation of a strand of hair utilizing one of the gripping handles.

Assuming that the needle has been secured to the handle 20 as shown in FIG. 4 of the drawings it is merely necessary to insert the needle through the scalp S into the tissue T as shown in FIG. 12. This can be either accomplished by raising a wheal or welt as shown in FIG. 12 manually or by introducing a chemical agent, or without doing so as shown in FIG. 13.

Both methods are believed workable, but production of the wheal or welt will facilitate insertion of the needle and insure deeper penetration.

In any event, it will be noted that the base 101 of the strand 100 will have been moved to the left of FIG. 12 following the path of insertion of the needle 10.

Figure 13:
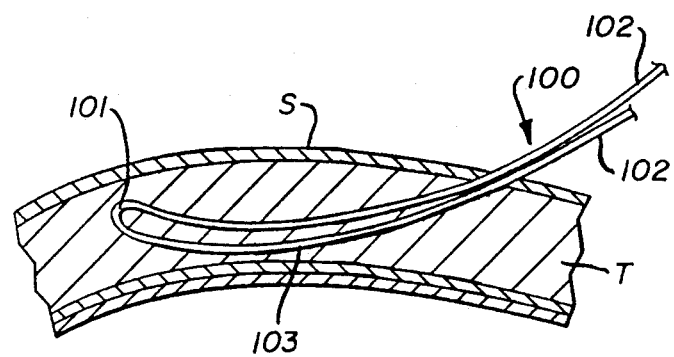
FIG. 13 is a view similar to FIG. 12.
Figure 14:
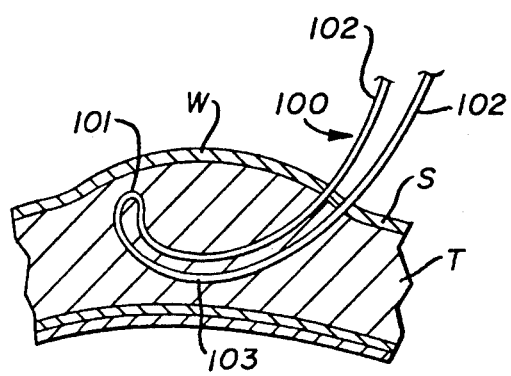
FIG. 14 is a view similar to FIG. 12 following removal of the needle.

The needle 10 can then be withdrawn so that the strand will be positioned as shown in FIGS. 13 and 14. In this regard, the curvature of the needle will insure that the base 101 of the looped strand is disposed fairly close to the scalp and that the lower part 103 of the loop will be disposed relatively far away from the scalp so that in effect a concave condition is created relative to the surface of the scalp. This will assist in retention of the hair since it will tend to resist removal inadvertently thereof. Also the projecting ends 102,102 of the hair will assume a more natural position comparable to that of natural hair.

It is assumed that normally there will be no difficulties with the strand 100 remaining in place upon removal of the needle 10.

However, the form of the invention illustrated in FIGS. 8 through 10 is intended to insure that this does happen.

In this form of the invention and assuming insertion to the position of FIG. 12 for example, it is simply necessary to move the movable handle 251 to the left compressing the spring and forcing the wire 250 out through the hollow needle until it emerges into the notch and comes into contact with the strand. The wire will force the strand out of the notch and insure that it was not inadvertantly hooked or snagged on the needle during retraction of the same.

In this regard, of course, a hollow needle 110 would be employed rather than a needle 10.

It is also possible, utilizing the form of the invention illustrated in FIGS. 6 and 7, to insert a tissue adhesive or a hemostatic agent into the tissue and about the strand 100. In this regard, assuming that a hollow needle 110 and the handle 120 of FIGS. 6 and 7 were employed and inserted to the position illustrated in FIG. 12, it is then merely necessary to activate the source of fluid which will pass through tubing 130, passage 121a of the handle 120 and 116 of the needle 110 and be expelled adjacent the notch 114 so that this fluid will be distributed into the tissue and assist in the healing and anchoring to the strand 100.

Figure 15:
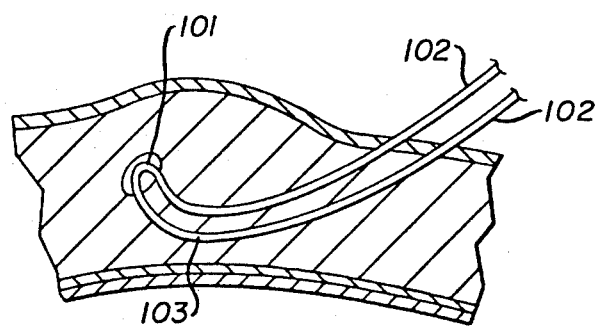
FIG. 15 is a view similar to FIG. 14 showing a modified form of the invention.

It is also possible, as illustrated in FIG. 15 to put tissue inert material or tissue adhesive on the base 101 of the loop prior to insertion in which event the hollow handle and hollow needle of FIGS. 6 and 7 would not be required.

Figure 17:
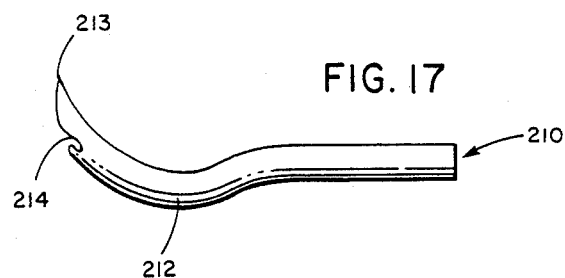
FIG. 17 is a partial perspective view showing the needle of FIG. 1 with the pocket on the lower or convex surface.
Figure 18:
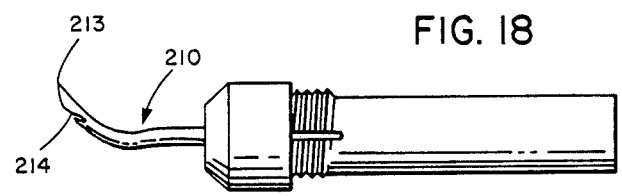
FIG. 18 is a view similar to FIG. 4 showing the needle of FIG. 17.
Figure 19:
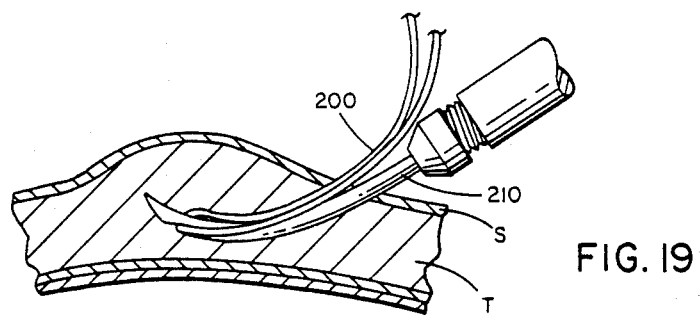
FIG. 19 is a view similar to FIG. 12 showing implantation of a strand of hair utilizing the needle of FIG. 17.

Turning next then to the modification of FIGS. 17 through 19, it has been discovered that the pockets or notches which engage the strands can be located anywhere about the circumference of the needle. FIGS. 1 through 16 illustrate the notch located on what may be described as the top or concave side or surface of the needle.

FIGS 17 through 19 illustrate the notch or pocket 214 disposed on the bottom or convex surface 212 of needle 210. Clinically, this has been found to be the most efficient location and is the preferred location.

It should be noted that FIG. 17 illustrates this modification on the solid needle of FIG. 1, but the preferred notch location is equally relevant to the hollow needle of FIG. 2.

The remaining apparatus illustrated and described herein as well as the method of operation alluded to remain applicable regardless of the notch location as can be seen from FIGS. 18 and 19.

While a full and complete description of the invention has been set forth in accordance with the dictates of the Patent Statutes, it should be understood that modifications can be resorted to without departing from the spirit hereof or the scope of the appended claims.

As noted earlier, in the preferred method the strand will be pre-formed to the condition of FIG. 16. However, due to the fact that the penetration path is arcuate or semilunar, the strand 100 will be placed in the tissue in the same configuration even if it is only formed as a loop when engaged with the needle. Under many circumstances this fact will be sufficient to achieve the objects of the invention.

It should also be noted that the instruments and apparatus illustrated and described herein can be utilized, as explained, regardless of whether the strand is pre-formed.

Finally, as noted herein, the notch or pocket can be disposed in various locations on the periphery of the needle. However, certain characteristics are believed to be important to all forms of the invention.

First, the pocket or notch should be located as close to the tip or point as possible. This will be dictated by the depth of the pocket necessary to engage or hold the thickness of the strand while still permitting enough wall thickness and strength to avoid breakage.

Second, the pocket or notch should angle rearwardly away from the tip as illustrated. This insures satisfactory engagement as the instrument penetrates and also facilitates disengagement upon removal of the instrument.

What is claimed is:

1. Apparatus for implanting replacement strands of hair in a human scalp, comprising:
   (A) an instrument having an elongate shank having first and second ends;
   (B) an arcuate penetration portion
      (1) projecting from said first end of said shank
      (2) terminating in a tapered, pointed distal end, and
      (3) having a strand receiving notch spaced from said distal end;
   (C) a gripping handle having first and second ends;
   (D) said first end of said handle being threaded;
   (E) a cap having a central aperture adapted to be slid over said instrument and being threaded for releasable engagement with said first end of said handle;
      (1) whereby said second end of said shank of said instrument is releasably engagable with said first end of said handle;
   (F) said gripping handle having
      (1) a passageway extending inwardly from said first end;
      (2) an axially extending opening in one peripheral surface spaced from said first end and radially communicating with said passageway;
      (3) a handle slidably received in said opening; and
      (4) a flexible stylet secured to said handle and received in said passageway; and
   (G) tension means received in said axially extending opening and normally urge said handle and said stylet toward said second end of said handle.

* * * * *